US012329899B2

(12) United States Patent
Yadidi

(10) Patent No.: US 12,329,899 B2
(45) Date of Patent: *Jun. 17, 2025

(54) DRY POWDER INHALER AND METHODS OF USE

(71) Applicant: Aspeya US Inc., Stamford, CT (US)

(72) Inventor: Kambiz Yadidi, Los Angeles, CA (US)

(73) Assignee: ASPEYA US INC., Stamford, CT (US)

(*) Notice: Subject to any disclaimer, the term of this patent is extended or adjusted under 35 U.S.C. 154(b) by 0 days.

This patent is subject to a terminal disclaimer.

(21) Appl. No.: 15/701,257

(22) Filed: Sep. 11, 2017

(65) Prior Publication Data

US 2018/0064890 A1 Mar. 8, 2018

Related U.S. Application Data

(63) Continuation of application No. 13/843,285, filed on Mar. 15, 2013, now Pat. No. 9,757,529, which is a continuation-in-part of application No. 13/791,734, filed on Mar. 8, 2013, now Pat. No. 9,757,395.

(60) Provisional application No. 61/740,407, filed on Dec. 20, 2012.

(51) Int. Cl.
*A61M 15/00* (2006.01)
*A61K 31/616* (2006.01)

(52) U.S. Cl.
CPC ....... *A61M 15/0045* (2013.01); *A61K 31/616* (2013.01); *A61M 2202/064* (2013.01)

(58) Field of Classification Search
CPC .............. A61M 15/00; A61M 15/0091; A61M 15/0065; A61M 15/0064; A61M 15/0021; A61M 15/0001; A61M 15/0002; A61M 15/0003; A61M 15/0004; A61K 9/0075
See application file for complete search history.

(56) References Cited

U.S. PATENT DOCUMENTS

| 3,906,950 A | 9/1975 | Cozza |
| 4,353,365 A | 10/1982 | Hallworth et al. |
| 4,885,287 A | 12/1989 | Hussain |
| 4,995,385 A | 2/1991 | Valentini et al. |

(Continued)

FOREIGN PATENT DOCUMENTS

| CN | 1388762 | 1/2003 |
| CN | 1491109 | 4/2004 |

(Continued)

OTHER PUBLICATIONS

Keller, Developments and trends in pulmonary drug delivery, Chemistry today, 1998.*

(Continued)

*Primary Examiner* — Joseph D. Boecker
(74) *Attorney, Agent, or Firm* — Oblon, McClelland, Maier & Neustadt, L.L.P.

(57) ABSTRACT

Methods for reducing the risk of a thromboembolic event, and a related drug delivery system are provided. In some embodiments, a dose of acetylsalicylic acid can be provided in powder form to a patient using a dry powder inhaler. The dose can be effective to reduce a risk of a thromboembolic event in a patient. A dry powder inhaler used for the method can have a mouthpiece, a reservoir for receiving the dose of acetylsalicylic acid, and an actuation member for making available the dose of acetylsalicylic acid for inhalation by a patient through the mouthpiece.

22 Claims, 2 Drawing Sheets

(56) References Cited

U.S. PATENT DOCUMENTS

| | | | | |
|---|---|---|---|---|
| 5,256,538 | A | 10/1993 | Aiken et al. | |
| 5,327,883 | A | 7/1994 | Williams et al. | |
| 5,366,967 | A * | 11/1994 | Bianco | A61K 45/06 514/59 |
| 5,506,203 | A | 4/1996 | Backstrom et al. | |
| 5,518,998 | A | 5/1996 | Backstrom et al. | |
| 5,639,441 | A | 6/1997 | Sievers et al. | |
| 5,673,686 | A | 10/1997 | Villax et al. | |
| 5,750,559 | A | 5/1998 | Bianco | |
| 5,855,913 | A | 1/1999 | Hanes et al. | |
| 5,874,064 | A | 2/1999 | Edwards et al. | |
| 5,875,776 | A * | 3/1999 | Vaghefi | A61M 15/0045 128/203.15 |
| 6,051,256 | A | 4/2000 | Platz et al. | |
| 6,051,566 | A | 4/2000 | Bianco | |
| 6,098,620 | A | 8/2000 | Lloyd et al. | |
| 6,136,295 | A | 10/2000 | Edwards et al. | |
| 6,136,346 | A | 10/2000 | Eljamal et al. | |
| 6,187,344 | B1 | 2/2001 | Eljamal et al. | |
| 6,254,854 | B1 | 7/2001 | Edwards et al. | |
| 6,257,233 | B1 * | 7/2001 | Burr | B05B 11/062 128/203.15 |
| 6,284,282 | B1 | 9/2001 | Maa et al. | |
| 6,309,623 | B1 | 10/2001 | Weers et al. | |
| 6,358,530 | B1 | 3/2002 | Eljamal et al. | |
| 6,408,846 | B1 | 6/2002 | Ohki et al. | |
| 6,423,344 | B1 | 7/2002 | Platz et al. | |
| 6,455,028 | B1 | 9/2002 | Wulffhart et al. | |
| 6,503,480 | B1 | 1/2003 | Edwards et al. | |
| 6,516,950 | B1 * | 2/2003 | Robertson | A61J 7/0076 206/534 |
| 6,561,186 | B2 | 5/2003 | Casper et al. | |
| 6,565,885 | B1 | 5/2003 | Tarara et al. | |
| 6,569,406 | B2 | 5/2003 | Stevenson et al. | |
| 6,592,904 | B2 | 7/2003 | Platz et al. | |
| 6,630,169 | B1 | 10/2003 | Bot et al. | |
| 6,638,495 | B2 | 10/2003 | Weers et al. | |
| 6,652,837 | B1 | 11/2003 | Edwards et al. | |
| 6,705,313 | B2 | 3/2004 | Niccolai | |
| 6,732,732 | B2 | 5/2004 | Edwards et al. | |
| 6,737,042 | B2 | 5/2004 | Rabinowitz et al. | |
| 6,766,799 | B2 | 7/2004 | Edwards et al. | |
| 6,848,197 | B2 | 2/2005 | Chen et al. | |
| 6,880,555 | B1 | 4/2005 | Brunnberg et al. | |
| 6,881,398 | B2 | 4/2005 | Myrman et al. | |
| 6,884,794 | B2 | 4/2005 | Staniforth et al. | |
| 6,893,657 | B2 | 5/2005 | Roser et al. | |
| 6,979,437 | B2 | 12/2005 | Bartus et al. | |
| 6,994,842 | B2 | 2/2006 | Lee et al. | |
| 6,998,137 | B2 | 2/2006 | Shih et al. | |
| 7,025,059 | B2 | 4/2006 | Pera | |
| 7,089,934 | B2 | 8/2006 | Staniforth et al. | |
| 7,146,978 | B2 | 12/2006 | Edwards et al. | |
| 7,189,750 | B2 | 3/2007 | Assaf et al. | |
| 7,201,929 | B1 | 4/2007 | Finkelstein | |
| 7,205,343 | B2 | 4/2007 | Dellamary et al. | |
| 7,267,813 | B2 | 9/2007 | Watanabe et al. | |
| 7,278,425 | B2 | 10/2007 | Edwards et al. | |
| 7,284,553 | B2 | 10/2007 | Hochrainer | |
| 7,306,787 | B2 | 12/2007 | Tarara et al. | |
| 7,405,207 | B2 | 7/2008 | Leonard et al. | |
| 7,431,916 | B2 | 10/2008 | Nilsson et al. | |
| 7,435,720 | B2 | 10/2008 | Quay et al. | |
| 7,516,741 | B2 | 4/2009 | Glusker et al. | |
| 7,521,068 | B2 | 4/2009 | Bosch et al. | |
| 7,534,914 | B2 | 5/2009 | Koike et al. | |
| 7,541,022 | B2 | 6/2009 | Staniforth et al. | |
| 7,556,035 | B2 | 7/2009 | Young et al. | |
| 7,556,798 | B2 | 7/2009 | Edwards et al. | |
| 7,559,325 | B2 | 7/2009 | Dunkley et al. | |
| 7,628,978 | B2 | 12/2009 | Weers et al. | |
| 7,651,770 | B2 | 1/2010 | Berkland et al. | |
| 7,669,596 | B2 | 3/2010 | Alston | |
| 7,682,614 | B2 | 3/2010 | Strober et al. | |
| 7,744,906 | B2 | 6/2010 | Coates | |
| 7,790,145 | B2 | 9/2010 | Weers et al. | |
| 7,806,117 | B2 | 10/2010 | Tsutsui | |
| 7,878,193 | B2 | 2/2011 | Kladders et al. | |
| 7,919,119 | B2 | 4/2011 | Straub et al. | |
| 7,954,491 | B2 | 6/2011 | Hrkach | |
| 8,069,851 | B2 | 12/2011 | Dunkley et al. | |
| 8,075,919 | B2 | 12/2011 | Brown et al. | |
| 8,114,438 | B2 | 2/2012 | Pipkin et al. | |
| 8,168,223 | B1 | 5/2012 | Tarara et al. | |
| 8,173,168 | B2 | 5/2012 | Platz et al. | |
| 8,201,555 | B2 | 6/2012 | Chawla | |
| 8,236,786 | B2 | 8/2012 | Finch et al. | |
| 8,246,934 | B2 | 8/2012 | Weers et al. | |
| 8,530,463 | B2 | 9/2013 | Cartt et al. | |
| 8,561,609 | B2 | 10/2013 | Donovan et al. | |
| 8,623,419 | B2 | 1/2014 | Malakhov et al. | |
| 8,771,744 | B2 | 7/2014 | Ruecroft et al. | |
| 8,790,648 | B2 | 7/2014 | Tocker et al. | |
| 8,795,634 | B2 | 8/2014 | Illum et al. | |
| 8,940,683 | B2 | 1/2015 | Levitt | |
| 8,985,102 | B2 | 3/2015 | Hodson et al. | |
| 8,997,799 | B2 | 4/2015 | Hodson et al. | |
| 9,051,302 | B2 | 6/2015 | Winssinger et al. | |
| 9,061,352 | B2 | 6/2015 | Lipp et al. | |
| 9,085,632 | B2 | 7/2015 | Coates et al. | |
| 9,101,539 | B2 | 8/2015 | Nagata et al. | |
| 9,125,999 | B2 | 9/2015 | Rolfs et al. | |
| 9,138,407 | B2 | 9/2015 | Caponetti et al. | |
| 2002/0025917 | A1 | 2/2002 | Pappalardo | |
| 2002/0033174 | A1 * | 3/2002 | Lecourt | A61K 9/124 128/200.23 |
| 2002/0094318 | A1 * | 7/2002 | Lee | A61K 9/145 514/23 |
| 2002/0128179 | A1 * | 9/2002 | Tacon | A61K 9/0073 424/489 |
| 2002/0158150 | A1 * | 10/2002 | Matsugi | A61M 15/0065 239/418 |
| 2003/0000518 | A1 * | 1/2003 | Rabinowitz | A61K 31/165 128/200.14 |
| 2003/0176421 | A1 | 9/2003 | Watson et al. | |
| 2003/0186843 | A1 | 10/2003 | Staniforth et al. | |
| 2003/0232019 | A1 | 12/2003 | Basu et al. | |
| 2004/0024013 | A1 * | 2/2004 | Asai | A61P 7/02 514/165 |
| 2004/0024057 | A1 * | 2/2004 | Earl | A61P 27/06 558/488 |
| 2004/0049022 | A1 | 3/2004 | Nyce et al. | |
| 2004/0092470 | A1 | 5/2004 | Leonard et al. | |
| 2004/0105821 | A1 | 6/2004 | Bernstein et al. | |
| 2004/0156790 | A1 * | 8/2004 | Rabinowitz | A61K 31/53 424/46 |
| 2004/0206350 | A1 | 10/2004 | Alston et al. | |
| 2004/0235802 | A1 * | 11/2004 | Gimona | A61K 45/06 514/165 |
| 2005/0000518 | A1 | 1/2005 | Dunkley et al. | |
| 2005/0004079 | A1 | 1/2005 | Benjamin et al. | |
| 2005/0084528 | A1 | 4/2005 | Saeed et al. | |
| 2005/0148555 | A1 | 7/2005 | Gupta et al. | |
| 2005/0180926 | A1 | 8/2005 | Lecourt et al. | |
| 2005/0249697 | A1 | 11/2005 | Uhrich et al. | |
| 2006/0002995 | A1 | 1/2006 | Harwigsson | |
| 2006/0030550 | A1 | 2/2006 | Lithgow et al. | |
| 2006/0257987 | A1 | 11/2006 | Gonzalez Valcarcel et al. | |
| 2006/0293217 | A1 | 12/2006 | Barker et al. | |
| 2007/0021382 | A1 | 1/2007 | Assaf | |
| 2007/0072939 | A1 | 3/2007 | Kupper | |
| 2007/0116761 | A1 | 5/2007 | Desai et al. | |
| 2007/0123477 | A1 * | 5/2007 | Malcolmson | A61K 9/1694 514/28 |
| 2007/0123571 | A1 | 5/2007 | Raj et al. | |
| 2007/0160661 | A1 * | 7/2007 | Finkelstein | A61K 31/495 424/754 |
| 2007/0178166 | A1 | 8/2007 | Bernstein et al. | |
| 2007/0232575 | A1 | 10/2007 | Baulieu et al. | |
| 2008/0066741 | A1 | 3/2008 | LeMahieu et al. | |
| 2008/0127972 | A1 * | 6/2008 | Morton | A61K 31/55 128/203.15 |
| 2008/0226736 | A1 | 9/2008 | Caponetti et al. | |

(56) References Cited

U.S. PATENT DOCUMENTS

| | | | |
|---|---|---|---|
| 2008/0306033 A1* | 12/2008 | Franzone | A61K 31/235 514/159 |
| 2009/0011030 A1 | 1/2009 | Jouhikainen et al. | |
| 2009/0110679 A1 | 4/2009 | Li et al. | |
| 2009/0136561 A1 | 5/2009 | Von Rechenberg et al. | |
| 2009/0220435 A1 | 9/2009 | Quay et al. | |
| 2009/0308392 A1 | 12/2009 | Smutney et al. | |
| 2009/0312380 A1 | 12/2009 | Becker | |
| 2010/0108058 A1* | 5/2010 | Glusker | A61M 15/0028 128/200.14 |
| 2010/0132705 A1 | 6/2010 | De Vos | |
| 2010/0158819 A1 | 6/2010 | Kligerman et al. | |
| 2010/0168710 A1 | 7/2010 | Braithwaite | |
| 2010/0234442 A1 | 9/2010 | Duarte-Vazquez et al. | |
| 2010/0242960 A1 | 9/2010 | Zangerle | |
| 2010/0258118 A1 | 10/2010 | Morton | |
| 2010/0316724 A1 | 12/2010 | Whitfield et al. | |
| 2010/0319694 A1 | 12/2010 | Cook et al. | |
| 2011/0112134 A1 | 5/2011 | Hutchinson et al. | |
| 2011/0123626 A1* | 5/2011 | Weers | A61P 31/00 514/61 |
| 2011/0142914 A1 | 6/2011 | Persaud et al. | |
| 2011/0146678 A1 | 6/2011 | Ruecroft et al. | |
| 2011/0166133 A1 | 7/2011 | Albaugh et al. | |
| 2011/0189106 A1 | 8/2011 | Danzig et al. | |
| 2011/0250130 A1 | 10/2011 | Benatuil et al. | |
| 2011/0263610 A1 | 10/2011 | Wan et al. | |
| 2011/0277752 A1 | 11/2011 | Cheu et al. | |
| 2012/0017892 A1* | 1/2012 | Ludwig | A61P 31/00 514/159 |
| 2012/0046251 A1 | 2/2012 | Schaefer et al. | |
| 2012/0064126 A1 | 3/2012 | Sung et al. | |
| 2012/0125325 A1 | 5/2012 | Bannister et al. | |
| 2012/0132203 A1 | 5/2012 | Hodson et al. | |
| 2012/0145150 A1 | 6/2012 | Donovan et al. | |
| 2012/0152245 A1 | 6/2012 | Rolfs et al. | |
| 2012/0263680 A1 | 10/2012 | Lander et al. | |
| 2012/0276193 A1 | 11/2012 | Graversen et al. | |
| 2012/0291780 A1 | 11/2012 | Donovan et al. | |
| 2012/0308566 A1 | 12/2012 | Martin et al. | |
| 2012/0309809 A1 | 12/2012 | Green et al. | |
| 2013/0004969 A1 | 1/2013 | Peschon et al. | |
| 2013/0028942 A1 | 1/2013 | Surber et al. | |
| 2013/0213397 A1* | 8/2013 | Curtis | A61M 15/0045 128/203.15 |
| 2013/0316001 A1 | 11/2013 | Popov et al. | |
| 2014/0065219 A1* | 3/2014 | Bosch | A61K 31/46 514/304 |
| 2014/0079784 A1 | 3/2014 | Burnier et al. | |
| 2014/0174437 A1 | 6/2014 | Yadidi | |
| 2014/0174440 A1 | 6/2014 | Yadidi | |
| 2014/0213560 A1 | 7/2014 | Vakkalanka | |
| 2014/0234330 A1 | 8/2014 | Budelsky et al. | |
| 2014/0239525 A1 | 8/2014 | McConville et al. | |
| 2014/0242174 A1 | 8/2014 | Walker | |
| 2014/0322238 A1 | 10/2014 | Budelsky et al. | |
| 2014/0322328 A1 | 10/2014 | Yadidi | |
| 2014/0364837 A1 | 12/2014 | Boyes et al. | |
| 2015/0005230 A1 | 1/2015 | Eliasof | |
| 2015/0045332 A1 | 2/2015 | Swenson | |
| 2015/0050713 A1 | 2/2015 | Malakhov et al. | |
| 2015/0059746 A1 | 3/2015 | Green | |
| 2015/0093338 A1 | 4/2015 | Farber | |
| 2015/0132386 A1 | 5/2015 | Heng et al. | |
| 2015/0136130 A1 | 5/2015 | Dehaan et al. | |
| 2015/0224129 A1 | 8/2015 | Trottein et al. | |
| 2015/0239866 A1 | 8/2015 | Machacek et al. | |
| 2015/0239966 A1 | 8/2015 | Baciu et al. | |
| 2015/0239987 A1 | 8/2015 | Liang et al. | |
| 2015/0284381 A1 | 10/2015 | Andresen et al. | |
| 2015/0320694 A1 | 11/2015 | Gu et al. | |
| 2015/0322070 A1 | 11/2015 | Rao et al. | |

FOREIGN PATENT DOCUMENTS

| | | | |
|---|---|---|---|
| CN | 102058886 | 5/2011 | |
| EP | 0499143 A2 * | 8/1992 | A61K 31/19 |
| EP | 1177805 | 2/2002 | |
| EP | 1238680 | 9/2002 | |
| EP | 1350511 | 10/2003 | |
| EP | 1814521 | 8/2007 | |
| EP | 1350511 B1 | 9/2008 | |
| GB | 2434754 | 8/2007 | |
| JP | H4-500070 | 1/1992 | |
| JP | 2002255814 | 9/2002 | |
| JP | 2003525081 | 8/2003 | |
| JP | 2004-509141 | 3/2004 | |
| JP | 2009-537199 | 10/2009 | |
| WO | WO 93/00951 | 1/1993 | |
| WO | WO 95/11666 | 5/1995 | |
| WO | 9737708 A1 | 10/1997 | |
| WO | 2000027359 | 5/2000 | |
| WO | WO 2002/024158 | 3/2002 | |
| WO | 03047598 | 6/2003 | |
| WO | 03047628 | 6/2003 | |
| WO | 2005040163 | 5/2005 | |
| WO | 2005041886 | 5/2005 | |
| WO | 2006017354 | 2/2006 | |
| WO | 2007072503 | 6/2007 | |
| WO | 2009089822 | 7/2009 | |
| WO | 2012061902 | 5/2012 | |
| WO | 2012107364 | 8/2012 | |
| WO | 2012107765 | 8/2012 | |
| WO | 2013004999 | 1/2013 | |
| WO | 2014131851 | 9/2014 | |
| WO | 2014155103 | 10/2014 | |
| WO | 2015002703 | 1/2015 | |
| WO | 2015011244 | 1/2015 | |
| WO | 2015054574 | 4/2015 | |
| WO | 2015127315 | 8/2015 | |
| WO | 2015148415 | 10/2015 | |
| WO | 2015153838 | 10/2015 | |
| WO | 2015155544 | 10/2015 | |

OTHER PUBLICATIONS

Miser, Appropriate use for primary prevention of cardiovascular disease, Editorials: controversies in family medicine 2011.*

Kallmann et al., Effects of low doses of aspirin, 10 mg and 30 mg daily, on bleeding time, thromboxane production and 6-keto PGF1 alpha excretion in healthy subjects, Thromb Res, 1987.*

WebMD, Heart attack signs, symptoms and emergency treatment 2011.*

Eikelboom et al., Antiplatelet Drugs: Antithrombotic Therapy and Prevention of Thrombosis, 9th ed: American College of Chest Physicians Evidence-Based Clinical Practice Guidelines, Chest, vol. 141, Issue 2, Supplement, 2012, pp. e89S-e119S, ISSN 0012-3692, https://doi.org/10.1378/chest. 11-2293.*

Diener et al., European Stroke Prevention Study 2. Dipyridamole and acetylsalicylic acid in the secondary prevention of stroke, Journal of the Neurological Sciences, vol. 143, Issues 1-2, 1996, pp. 1-13, ISSN 0022-510X, https://doi.org/10.1016/S0022-510X(96)00308-5.*

Algra, et al., "Aspirin at Any Dose Above 30 mg Offers Only Modest Protection After Cerebral Ischaemia," J of Neurology, Neurosurgery & Psychiatry, 1996, 60:197-199.

Asprin Dosage-Drugs, www.druigs.com, Dec. 2011.

"Aspirin", Martindale: The Complete Drug Reference, 33rd ed., 2002 Pharmaceutical press, pp. 14-18.

ATT Collaboration, "Aspirin in the Primary and Secondary Prevention of Vascular Disease: Collaborative Meta-Analysis of Individual Participant Data from Randomised Trials," The Lancet, 2009, 373:1849-1860.

Awa, et al., "Prediction of time-dependent interaction of aspirin with ibuprofen using a pharmacokinetic/pharmacodynamics model," Journal of Clinical Pharmacy and Therapeutics, 2012, vol. 37, pp. 469-474.

(56) References Cited

OTHER PUBLICATIONS

Boysen, et al., "Danish Very-low-dose Aspirin After Carotid Endarterectomy Trial," Stroke, 1988, 19:1211-1215.
Chew, et al., "The Role of Particle Properties in Pharmaceutical Powder Inhalation Formulations," Journal of Aerosol Medicine, 2002, vol. 15, No. 3, pp. 325-330.
Christen, et al., "Low-dose Aspirin and Risk of Cataract and Subtypes in a Randomized Trial of U.S. Physicians" Ophthalmic Epidemiology, 1998, vol. 5, No. 3, pp. 133-142.
European Search Report dated Jul. 18, 2016 corresponding to European Application No. 13864747.4; 6 pages.
Fehri, et al., "Bioavailability of Acetylsalicylic Acid Administered Orally or Rectally in the Rabbit," J. Pharma Belg, 1989, vol. 44, No. 1, pp. 5-10.
Geller, et al., "Development of an Inhaled Dry-Powder Formulation of Tobramycin Using PlumoSphere Technology," J Aerosol Med Pulm Drug Deliv, Aug. 2011, 24(4), pp. 175-182.
Hadinoto et al., "Drug Release Study of Large Hollow Nanoparticulate Aggregates Carrier Particles for Pulmonary Delivery," International Journal of Pharmaceutics 341 (2007) 195-206.
Hadinoto, et al., "Dry powder aerosol delivery of large hollow nanoparticulate aggregates as prospective carriers of nanoparticulate drugs: Effects of phospholipids," International Journal of Pharmaceuticals, Oct. 2006, 33: 187-198.
Hovens et al., Aspirin in the prevention and treatment of venous thromboembolism, Journal of Thrombosis and Haemostasis, 2006; 4: 1470-5.
Hovione TwinCaps Dry Powder Inhaler, <http://www.hovione.com/twincaps/twincaps.asp>, visited Aug. 2013.
Hovione—Particle Design Technologies, <http://www.hovione.com/pd/particledesigntechnologies.asp>, visited Aug. 2013.
"Internal Analgesic: Antipyretic, and Antirheumatic Drug Products for Over-the-Counter Human Use: Final Rule for Professional Labeling of Aspirin, Buffered Aspirin, and Aspirin in Combination with Antacid Drug Products," Federal Register, Oct. 23, 1998, vol. 63, No. 205, pp. 56802-56819.
Iwamoto, "Gastrointestinal and Hepatic First-Pass Metabolism of Aspirin in Rats," J Pharm Pharmacol. Mar. 1982; 34(3), pp. 176-180.
Jaffe, et al., "Recovery of Endothelial Cell Prostacyclin Production after Inhibition by Low Doses of Aspirin," The American Society for Clinical Investigation, Inc., Mar. 1979, vol. 63, pp. 532-535.
Kim, et al., "Airway Responsiveness to Inhaled Aspirin is Influenced by Airway Hyperresponsiveness in Asthmatic Patients," Korean J Intern Med, Sep. 2010; 25(3): 309-316.
Kupczyk, et al. "Lipoxin A4 Generation Is Decreased in Aspirin-Sensitive Patients in Lysine-Aspirin Nasal Challenge in Vivo Model", Allergy (Oxford, United Kingdom) (2009), 64(12), 1746-1752.
Kurth, et al., "Inhibition of Clinical Benefits of Aspirin on First Myocardial Infarction by Nonsteroidal Antiinflammatory Drugs," Circulation, 2003, 108:1191-1195.
Miser, Appropriate Aspirin Use for Primary Prevention of Cardiovascular Disease, Editorials: Controversies in Family Medicine, 2011.
Phillips et al., "Inhaled Lysine-Aspirin as a Bronchoprovocation Procedure in Aspirin-Sensitive Asthma: its Repeatability, Absence of a Late-Phase Reaction, and the Role of Histamine," J Allergy Clin Immunol, Aug. 1989; 84(2):232-41.
Press release by Activaero GmbH, Dec. 19, 2006, <http://www.pharmaloco.com/news.sub.—detail/Activaero+and+Group+of+Researchers+Receive+Grant+for+Develop/14009/index.html>.
"Physicians' Health Study I," <http://phs.bwh.harvard.edu/phs1.htm>, Mar. 2009.
Rocca, et al., "Variability in the Responsiveness to Low-Dose Aspirin: Pharmacological and Disease-Related Mechanisms," Thrombosis, 2012, 11 pages.
Roth, et al., "Aspirin, Platelets, and Thrombosis: Theory and Practice," Blood, Feb. 15, 1994, vol. 83, No. 4, pp. 885-898.
Sestini et al., "Different Effects of Inhaled Aspirin-like Drugs on Allergen-Induced Early and Late Asthmatic Responses," Am J Respir Grit Care Med, Apr. 1, 1999 vol. 159 No. 4 1228-1233.
Sestini, et al., "Protective Effect of Inhaled Lysine Acetylsalicylate on Allergen-Induced Early and Late Asthmatic Reactions," J Allergy Clin Immunol, 1997 vol. 100, pp. 71-77.
Soleti et al., "Aspirin Inhalation Treatment for COPD Patients: Preliminary Studies on PK and Inflammatory Biomarkers," Thematic Poster Session, P825, Drug delivery and pharmacokinetics I, Sep. 25, 2011, p. 138s.
Sung, et al., "Nanoparticles for Drug Delivery to the Lungs," Trends in Biotechnology, 2007, vol. 25, No. 12.
The Dutch TIA Trial Study Group, "A Comparison of Two Doses of Aspirin (30 mg vs. 283 mg a day) in Patients After a Transient Ischemic Attack or Minor Ischemic Stroke," The New England Journal of Medicine, 1991, vol. 325, No. 18, pp. 1261-1266.
WebMD Heart Attack; 2011.
Canadian Intellectual Property Office, "First Office Action", for Canadian Application No. 2,895,398, dated Nov. 8, 2016, 4 pgs.
Canadian Intellectual Property Office, "Second Office Action", for Canadian Application No. 2,895,398, dated Sep. 27, 2017, 4 pgs.
European Patent Office, "Official Action (Article 94(3)) EPC", for EP13864747.4, dated Oct. 5, 2017, 4 pgs.
IP Australia, "First Examination Report", for AU 2013205497, dated Aug. 19, 2014, 4 pgs.
IP Australia, "Second Examination Report", for AU 2013205497, dated Nov. 9, 2015, 3 pgs.
IP Australia, "First Examination Report", for AU 2016213728, dated Oct. 12, 2017, 4 pgs.
Japanese Patent Office, "First Office Action" for JP 2015-549353 with English translation, dated Aug. 1, 2016 6 pgs.
Japanese Patent Office, "Second Office Action" for JP 2015-549353, dated Apr. 19, 2017, 5 pgs.
State Intellectual Property Office of China PRC, "First Office Action" for CN 201380073320.3 (English translation), dated Aug. 11, 2016, 6 pgs.
State Intellectual Property Office of China PRC, "Second Office Action" for CN 201380073320.3 with partial English translation, dated May 3, 2017, 6 pgs.
USPTO, "International Search Report and Written Opinion" for international application No. PCT/US2013/032597, dated Jun. 11, 2013, 7 pgs.
Office Action dated Nov. 3, 2016, in co-pending U.S. Appl. No. 13/791,734.
Stroke Prevention in Atrial Fibrillation Investigators ("Risk factors for thromboembolism during aspirin therapy in patients with atrial fibrillation: the stroke prevention in atrial fibrillation study", J Stroke Cerebrovasc Dis, 5 (1995), pp. 147-157, https://doi.org/10.1016/S1052-3057(10)80166-1).
Aspirin the mighty drug (year 2007).
Barnett et al., Aspirin Dose in Stroke Prevention, Stroke, 1996; 27:588.
Office Actions dated Dec. 8, 2021, in co-pending U.S. Appl. No. 16/370,932.
Office Actions dated Apr. 27, 2023, in co-pending U.S. Appl. No. 16/370,932.
Office Action with a mailing date of Jun. 30, 2016 on the corresponding Japanese Patent Application No. 2015-549353 (with Machine English translation).
Office Action with a mailing date of Mar. 22, 2018 on the corresponding Japanese Patent Application No. 2015-549353 (with Machine English translation).
Notice of Allowance with a mailing date of Sep. 5, 2018 on the corresponding Japanese Patent Application No. 2015- 549353 (with Machine English translation).
Office Action with a mailing date of May 3, 2017 on the corresponding Chinese Patent Application No. 201380073320.3 (with Machine English translation).
Extended European Search Report with a mailing date of Sep. 29, 2023, issued in corresponding Application No. EP 23 16 4415.4 (reference 24 cited therein).
Anne Van Hecken, PhD et al.; "Comparative Inhibitory Activity of Rofecoxib, Meloxicam, Diclofenac, Ibuprofen, and Naproxen on

(56) References Cited

OTHER PUBLICATIONS

COX-2 versus COX-1 in Healthy Volunteers", The Journal of Clinical Pharmacology, Lippincott Co, Hagerstown, Md, US, vol. 40, No. 10, Oct. 1, 2000 (Oct. 1, 2000), pp. 1109-1120.

Patrono, C. et al., "Low-Dose Aspirin for the Prevention of Atherothrombosis", New England Journal of Medicine, 2005, pp. 2373-2383.

Swarbrick, J., "Encyclopedia of Pharmaceutical Technology", New York, USA: Informa Healthcare, 2007, Ed. Third—pp. 1279-1286 and cover pages.

Dai, Y et al., "Clinical Use of Aspirin in Treatment and Prevention of Cardiovascular Disease", Thrombosis, vol. 2012, Article ID 245037, 2021, pp. 1-7.

British National Formulary "British National Formulary 61" BMJ Group and Pharmaceutical Press, 2011 - pp. 149-152 and cover pages.

Patentee's letter dated Mar. 9, 2021, and enclosure "Exhibit C" filed during examination, 8 pages.

Aulton M.E., "Pharmaceutics: The Science of Dosage Form Design", Churchill Livingstone, 2022, Ed. Second, 18 pages.

Proof of online publication of D5 on Nov. 24. 2011, available from: https://www.ncbi.nlm.nih.gov/pms/articles/PMC3236445.

\* cited by examiner

DRY POWDER INHALER AND METHODS OF USE

CROSS-REFERENCE TO RELATED APPLICATION(S)

This application is a continuation of U.S. application Ser. No. 13/843,285, filed Mar. 15, 2013, which is a continuation-in-part of U.S. application Ser. No. 13/791,734, filed Mar. 8, 2013, which claims the benefit of U.S. Provisional Application No. 61/740,407, filed Dec. 20, 2012, all of which are incorporated herein by reference in their entirety.

FIELD

The subject technology relates generally to apparatuses and methods for delivery of substances, e.g., delivery of medication to the lungs using by inhalation for treating disease.

SUMMARY

An aspect of at least one embodiment disclosed herein includes the recognition of a need for improved apparatuses and methods for delivery of drugs for treating disease that utilize a dosage that is effective to reduce a risk of a thromboembolic event in a patient, lower than traditional dosages, and administered using a more direct delivery mechanism to the systemic blood stream.

Thromboembolic Symptoms and Events

A thromboembolic event, such as myocardial infarction, deep venous thrombosis, pulmonary embolism, thrombotic stroke, etc., can present with certain symptoms that allow a patient or clinician to provide an initial therapy or treatment for the event. In some situations, an 81 mg, low dose, or baby aspirin or a regular aspirin (330 mg) may be orally administered in order to provide an initial treatment for the patient.

According to some embodiments disclosed herein is the realization that this treatment may not act as quickly as necessary to provide a sufficient therapeutic effect and therefore, may lead to a less preferred outcome. Thus, in some embodiments, a drug delivery system and related methods are disclosed that provide an accelerated and more efficient pathway and treatment for reducing the risk of a thromboembolic event and/or providing treatment for a thromboembolic event. For example, some embodiments provide systems and methods of administering a nonsteroidal anti-inflammatory drug ("NSAID") by inhalation, such as by a dry powder inhaler ("DPI") or a metered dose inhaler ("MDI").

Delivery Mechanisms for Drugs

Drugs can be administered orally in different ways, such as liquids, capsules, tablets, or chewable tablets. The oral route is used most often because it is the most convenient, safest, and least expensive. However, oral drug delivery has limitations because of the way a drug typically moves through the digestive tract.

For example, when a drug is administered orally, it is absorbed in the mouth, stomach, and the small intestine. Before the drug enters the bloodstream, it must pass through the intestinal wall and travels to the liver. While passing through the intestinal wall and liver, the drug is metabolized, which can decrease the amount of the drug that actually reaches the bloodstream. The metabolism of the drug reduces the bioavailability of the drug and is often termed the "first pass effect." The fraction of the drug lost during due to the first pass effect is generally determined by absorption in the liver and gut wall, and gastrointestinal lumen enzymes, gut wall enzymes, bacterial enzymes, and hepatic (liver) enzymes.

Generally, the first pass effect on aspirin significantly reduces the bioavailability of the administered dosage. For example, due to the acidic conditions in the stomach, aspirin is absorbed in the stomach and the upper small intestine. After being absorbed, aspirin is metabolized to acetic acid and salicylate. When taken orally, generally only about one to two-thirds of the dose of aspirin is bioavailable due to the first pass effect.

For example, in Iwamoto K., GASTROINTESTINAL AND HEPATIC FIRST-PASS METABOLISM OF ASPIRIN IN RATS, J Pharm Pharmacol. 1982 Mar; 34(3), pp. 176-80, the entirety of which is incorporated herein by reference, the study examines the absorption of aspirin in four male subjects following an oral solution of 650 mg. As stated in the study report, "the absorption process appeared to follow first-order kinetics, with a half-life ranging from 4.5 to 16.0 min. between subjects. Comparison of the area under the aspirin plasma concentration-time curve following intravenous and oral routes indicated that only 68% of the dose reached the peripheral circulation intact."

The applicant has determined that even drugs that are administered by inhalation undergo a first pass effect. For drug administration by inhalation, smaller particles proceed via a nasal route, down the windpipe (trachea) and into the lungs. The size of the particles can be determinative of the overall efficacy of the treatment. Once inside the lungs, these particles are absorbed into the bloodstream.

Few drugs are administered by inhalation because the dosage of an inhaled drug, as well as the delivery timing, can often be difficult to measure. Usually, this method is used to administer drugs that act specifically on the lungs, such as aerosolized antiasthmatic drugs in metered-dose containers, and to administer gases used for general anesthesia.

Pharmacokinetics of Aspirin

Aspirin is the acetylated form of salicylic acid, and the active chemical in aspirin is called acetylsalicylic acid (ASA). Aspirin is used by millions of people to achieve desirable effects, and by many people, baby aspirin is often used daily. The principal effect of aspirin is to impair the function of cyclooxygenase enzymes (specifically, COX1 and COX2 enzymes).

By inhibiting COX 1, aspirin can irreversibly inhibit platelet aggregation, which decreases the risk of blood clots. Additionally, the impairment of the COX2 enzyme can reduce inflammation, stiffness, and pain in the body by inhibiting prostaglandins and thromboxanes. As such, individuals at high risk for heart attack, stroke, or with inflammation often take aspirin to address symptoms and effects of these conditions. As noted, aspirin can effectively reduce the likelihood of such myocardial events and reduce pain and inflammation with a dose as small as a baby aspirin. However, due at least in part to its inhibition of COX1, aspirin can increase the risk of bleeding and cause damage to organs such as the stomach and intestines, which can be painful.

Dry Powder Inhaler Technology

As stated above, the oral delivery of aspirin may create a risk of damage to the stomach wall leading to pain, indigestion and a high risk of bleeding. Further, according to at least one of the aspects of embodiments disclosed herein is the realization that it is often difficult to orally administer a drug during emergency situations that may implicate or result in a thromboembolic event. For example, the patient may be experiencing vomiting or otherwise be unable to take the drug orally. Additionally, oral administration of a drug may be undesirable because the drug does not reach the systemic blood stream immediately, thus delaying the important effects of the drug. Even so, due to the first pass effect in the liver and gut, the amount of drug reaching systemic circulation is much less than that administered. Therefore, according to aspects of various embodiments disclosed herein is the realization that an alternative route of administration could avoid these unwanted side-effects.

Various embodiments disclosed herein reflect the novel realization that delivery of a drug by inhalation in the early stages of an emergency situation can provide a fast-acting, effective form of preliminary treatment of certain medical conditions. For example, in some embodiments, upon receiving a complaint of a symptom of a serious thromboembolic event, a patient can be administered, by DPI, a therapeutic amount of a NSAID. The NSAID can address problems associated with or provide an initial treatment for the medical condition.

However, dry powder inhalation of drugs has generally been limited by cough, to dosages of less than a milligram. Recent developments in particle engineering, in particular the development of PulmoSphere™ technology, have enabled the delivery of a larger amount of dry powder to delivered to the lungs in a single actuation. See David E. Geller, M. D., et al., DEVELOPMENT OF AN INHALED DRY-POWDER FORMULATION OF TOBRAMYCIN USING PULMOSPHERE™ TECHNOLOGY, J Aerosol Med Pulm Drug Deliv. 2011 August; 24(4), pp. 175-82, the entirety of which is incorporated herein by reference. In this publication, a dose of 112 mg tobramycin (in four capsules) was effectively delivered via PulmoSpheres™.

In accordance with some embodiments is the realization that the body includes various particle filters that limit the efficacy of inhaled drugs. For example, the oropharynx tends to prevent passage of particles having a diameter greater than 5 μm. However, in order to reach the alveoli, particles must have a size from about 1 μm to about 5 μm. Accordingly, some embodiments herein disclose the preparation and use of inhalable aspirin using technology similar to PulmoSpheres™ to produce particles with a median geometric diameter of from about 1 μm to about 5 μm, and in some embodiments, from about 1. 7 μm to about 2.7 μm.

There has been no single dose use of aspirin by dry powder inhaler to replace the traditional daily use of a NSAID (such as a baby aspirin) or emergency use of a NSAID as preventative care for symptoms of a thromboembolic event. Accordingly, some embodiments disclosed herein provide methods for administering a NSAID by dry powder inhalation in an amount less than the dosage of a baby aspirin (e.g., less than 81 mg).

Therefore, in some embodiments, a method for treating disease, e.g., by reducing the risk of a thromboembolic event, can be provided, which comprises administering a NSAID, such as a salicylate, by a DPI or MDI. For example, the method can comprise administering acetylsalicylic acid by a DPI or MDI. The administered dosage can be less than 25 mg of acetylsalicylic acid. Further, the administered dosage can be less than 20 mg of acetylsalicylic acid. The administered dosage can be less than 15 mg of acetylsalicylic acid. The administered dosage can also be less than 12 mg of acetylsalicylic acid. The administered dosage can be less than 10 mg of acetylsalicylic acid. Furthermore, the administered dosage can be less than 8 mg of acetylsalicylic acid. The administered dosage can be less than 5 mg of acetylsalicylic acid. In some embodiments, the administered dosage can be less than 2 mg of acetylsalicylic acid.

For example, according to some embodiments, the dosage can be from about 2 mg to about 30 mg of acetylsalicylic acid. In some embodiments, the dosage can be from about 4 mg to about 25 mg of acetylsalicylic acid. The dosage can be from about 6 mg to about 20 mg of acetylsalicylic acid. Further, in some embodiments, the dosage can be from about 8 mg to about 15 mg of acetylsalicylic acid. Further, in some embodiments, the dosage can be from about 10 mg to about 13 mg of acetylsalicylic acid. For example, in some embodiments, the dosage can be about 1 mg, 2 mg, 3 mg, 4 mg, 5 mg, 6 mg, 7 mg, 8 mg, 9 mg, 10 mg, 11mg, 12 mg, 13 mg, 14 mg, 15 mg, 16 mg, 17 mg, 18 mg, 19 mg, or 20 mg of acetylsalicylic acid.

Additionally, the dose of acetylsalicylic acid can be less than about 80 mg. In some embodiments, the dose of acetylsalicylic acid can be from about 1 mg to about 75 mg. In some embodiments, the dose of acetylsalicylic acid can be from about 2 mg to about 60 mg. In some embodiments, the dose of acetylsalicylic acid can be from about 5 mg to about 40 mg. In some embodiments, the dose of acetylsalicylic acid can be from about 10 mg to about 30 mg. In some embodiments, the dose of acetylsalicylic acid can be from about 12 mg to about 25 mg. In some embodiments, the dose of acetylsalicylic acid can be from about 15 mg to about 20 mg.

In accordance with some embodiments, such dosages can provide a bioequivalent dosage when compared to typical dosages of 81 mg to about 325 mg, while demonstrating few negative side effects.

Thus, in some embodiments, a NSAID, such as aspirin, can be administered by DPI or MDI in a single dose that is much less than a traditional oral dose of aspirin, which can provide an bioequivalent equivalent treatment while tending to avoid the negative side effects associated with some NSAIDs, such as aspirin. Further, systems of administering such treatments are also provided.

The DPI or MDI can have a mouthpiece and an actuation member for making available the NSAID for inhalation by a patient to reduce the risk of the thromboembolic event.

For example, according to some embodiments, a method of reducing the risk of a thromboembolic event is provided and can comprise administering a dose of a nonsteroidal anti-inflammatory drug by a dry powder inhaler. The dose can be effective to reduce a risk of a thromboembolic event in a patient. The dry powder inhaler can have a mouthpiece and an actuation member for making available the dose of the nonsteroidal anti-inflammatory drug for inhalation by the patient to reduce the risk of the thromboembolic event.

A drug delivery system can also be provided according to some embodiments, for treating a disease, for example, by reducing the risk of a thromboembolic event. The system can comprise a dose of a nonsteroidal anti-inflammatory drug in powder form. The dose can be effective to reduce a risk of a thromboembolic event in a patient. The system can also comprise a dry powder inhaler. The dry powder inhaler can have a mouthpiece, a reservoir for receiving the dose of the nonsteroidal anti-inflammatory drug, and an actuation member for making available the dose of the nonsteroidal anti-inflammatory drug for inhalation by the patient through the mouthpiece.

In some embodiments, the thromboembolic event comprises at least one of myocardial infarction, deep venous thrombosis, pulmonary embolism, or thrombotic stroke. The dose of the nonsteroidal anti-inflammatory drug can be administered as a preliminary treatment in response to a symptom of a thromboembolic event. The nonsteroidal anti-inflammatory drug can comprise aspirin. Further, the dose of the nonsteroidal anti-inflammatory drug can be administered in a single dose.

Additional features and advantages of the subject technology will be set forth in the description below, and in part will be apparent from the description, or may be learned by practice of the subject technology. The advantages of the subject technology will be realized and attained by the structure particularly pointed out in the written description and claims hereof as well as the appended drawings.

It is to be understood that both the foregoing general description and the following detailed description are exemplary and explanatory and are intended to provide further explanation of the subject technology as claimed.

BRIEF DESCRIPTION OF THE DRAWINGS

The accompanying drawings, which are included to provide further understanding of the subject technology and are incorporated in and constitute a part of this specification, illustrate aspects of the subject technology and together with the description serve to explain the principles of the subject technology.

DETAILED DESCRIPTION

Figure 1:
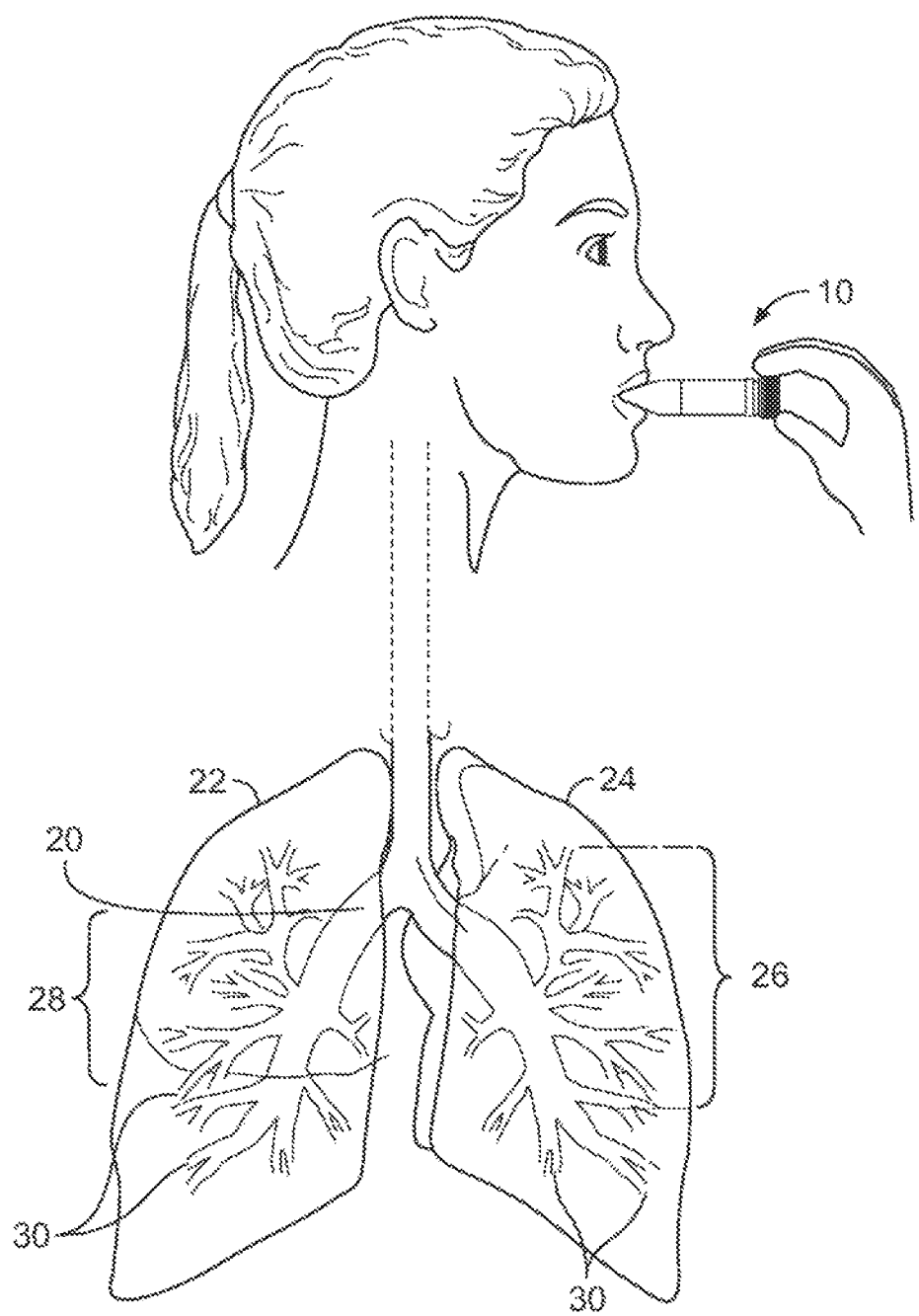
FIG. 1 is a schematic view of a patient using a dry powder inhaler, in accordance with some implementations of the methods and systems disclosed herein.

In the following detailed description, numerous specific details are set forth to provide a full understanding of the subject technology. It will be apparent, however, to one ordinarily skilled in the art that the subject technology may be practiced without some of these specific details. In other instances, well-known structures and techniques have not been shown in detail so as not to obscure the subject technology.

A phrase such as "an aspect" does not imply that such aspect is essential to the subject technology or that such aspect applies to all configurations of the subject technology. A disclosure relating to an aspect may apply to all configurations, or one or more configurations. An aspect may provide one or more examples of the disclosure. A phrase such as "an aspect" may refer to one or more aspects and vice versa. A phrase such as "an embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples of the disclosure. A phrase such "an embodiment" may refer to one or more embodiments and vice versa. A phrase such as "a configuration" does not imply that such configuration is essential to the subject technology or that such configuration applies to all configurations of the subject technology. A disclosure relating to a configuration may apply to all configurations, or one or more configurations. A configuration may provide one or more examples of the disclosure. A phrase such as "a configuration" may refer to one or more configurations and vice versa.

As discussed above, although NSAIDs, such as aspirin, can provide various beneficial effects and contribute to reducing the likelihood of a thromboembolic event, there may be some drawbacks to their use. Further, the use of NSAIDs, such as aspirin, in a clinical setting has traditionally been limited to oral administration. Oral administration of aspirin, for example, can result in the loss or inactivation of approximately ⅔ of the oral dosage due to the first pass effect in the gut and liver. While one third of the dosage reaches the systemic blood stream and provides the desired effect, the negative side effects created by the full dosage often deter patients from using aspirin on a regular or daily basis.

Further, in many situations, such as in emergencies, oral administration of NSAIDs, such as aspirin, may be inappropriate because it may take too long to be effective. According to at least one aspect of some embodiments disclosed herein is the realization that an alternative administration method and systems can be implemented that utilize a lower dosage and provide a more direct delivery mechanism to the systemic blood stream. Thus, some embodiments disclosed herein allow for the beneficial effects of NSAIDs, such as aspirin, to be achieved on a regular basis and in emergency situations, while minimizing previous drawbacks associated with the use of NSAIDs.

Various studies have determined that aspirin has a significant effect on reducing the risk of myocardial infarction. However, these studies presented inconclusive data on strokes, pulmonary embolism, or deep venous thrombosis. These studies have used aspirin dosages of 325 mg, However, these studies have based their findings on oral administration of aspirin and have not suggested DPI or MDI pathways, which are provided in some embodiments disclosed herein. Further, the administration of aspirin has negative side effects, such as significantly increasing major gastrointestinal and extracranial bleeds by over 50%. This has led some to argue that for preventative treatment, aspirin is of uncertain net value.

Further studies have tested whether the benefits of aspirin could be obtained at low dosages, such as that of baby aspirin (i.e., 81 mg). The Swedish Aspirin Low-dose Trial (SALT) found that a low dose (75 mg/day) of aspirin significantly reduces the risk of stroke or death in patients with cerebrovascular ischaemic events. However, the study also reported gastrointestinal side-effects that included a significant excess of bleeding episodes. A Danish study found that patients receiving aspirin as an antithrombotic agent achieved satisfactory platelet inhibition with 50 mg/day, while the remainder of the patients needed over 50 mg/day. Furthermore, a Dutch TIA Study concluded that aspirin at any dose above 30 mg daily prevents 13% of vascular events, and that there is a need for more efficacious drugs. However, no study or teaching has been provided regarding the administration of aspirin by DPI or MDI at very low doses.

Additionally, the applicant notes that although inhaled dry powder formulations of aspirin have been developed, reports have stated that the formulation was not clinically feasible because it is difficult to meet the high dosage requirements of aspirin (~80 mg/day for low-dose prevention of coronary events and stroke, and at least 300 mg/day for pain or fever relief) via pulmonary delivery of dry powders.

In addition, these reports recognize that adverse effects of dry powder on the lungs, such as coughing, cannot be avoided unless the doses are less than a few tenths of a milligram in a single breath. Thus, prior teachings suggest that higher dosage requirements of aspirin would be impossible to meet using DPI. Finally, some have taught that there is a higher incidence of aspirin intolerance in asthmatic patients when aspirin is delivered by inhalation than orally.

In yet another study, the authors noted that use of nanoparticulate drugs for dry powder inhaler (DPI) delivery is not straightforward. Direct inhalation of nanoparticulate drugs was infeasible due to their small size. The nanometer size leads to the nanoparticulate drugs being predominantly exhaled from the lungs, without any deposition taking place. Moreover, a severe aggregation problem arising from the small size makes their physical handling difficult for DPI delivery. Accordingly, "large hollow earner particles" of nanoparticulate drugs has been developed for pulmonary delivery of some drugs. See Hadinoto et al., *Drug Release Study Of Large Hollow Nanoparticulate Aggregates Carrier Particles For Pulmonary Delivery*, International Journal of Pharmaceutics 341 (2007) 195-20, the entirety of which is incorporated by reference herein.

In the Hadinoto study, the authors used aspirin as a model for "lowly watersoluble" drugs. The authors acknowledged that "with regard to the aspirin, the nanoparticulate polymer delivery method is not the most suitable method of delivery due to the high dosage requirement of aspirin (~300 mg/day)," and overall, the aim of the study was to identify key facets in the formulation of the large hollow nanoparticulate aggregates. See id.

In some embodiments of the inventions disclosed herein, methods and systems are provided for treating a disease, for example, by reducing the risk of a thromboembolic event by administration of a very low amount of a NSAID, such as a low dose of aspirin, by DPI or MDI. The dose can be much less than that of a baby aspirin (e.g., less than 81 mg). The administered dosage can be less than 25 mg of acetylsalicylic acid. Further, the administered dosage can be less than 20 mg of acetylsalicylic acid. The administered dosage can be less than 15 mg of acetylsalicylic acid. The administered dosage can also be less than 12 mg of acetylsalicylic acid. The administered dosage can be less than 10 mg of acetylsalicylic acid. Furthermore, the administered dosage can be less than 8 mg of acetylsalicylic acid. The administered dosage can be less than 5 mg of acetylsalicylic acid. In some embodiments, the administered dosage can be less than 2 mg of acetylsalicylic acid.

For example, according to some embodiments, the dosage can be from about 2 mg to about 30 mg. In some embodiments, the dosage can be from about 4 mg to about 25 mg of acetylsalicylic acid. The dosage can be from about 6 mg to about 20 mg of acetylsalicylic acid. Further, in some embodiments, the dosage can be from about 8 mg to about 15 mg of acetylsalicylic acid. Further, in some embodiments, the dosage can be from about 10 mg to about 13 mg of acetylsalicylic acid. For example, in some embodiments, the dosage can be about 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, or 20 mg of acetylsalicylic acid.

Additionally, the dose of acetylsalicylic acid can be less than about 80 mg. In some embodiments, the dose of acetylsalicylic acid can be from about 1 mg to about 75 mg. In some embodiments, the dose of acetylsalicylic acid can be from about 2 mg to about 60 mg. In some embodiments, the dose of acetylsalicylic acid can be from about 5 mg to about 40 mg. In some embodiments, the dose of acetylsalicylic acid can be from about 10 mg to about 30 mg. In some embodiments, the dose of acetylsalicylic acid can be from about 12 mg to about 25 mg. In some embodiments, the dose of acetylsalicylic acid can be from about 15 mg to about 20 mg.

Such dosages can provide a bioequivalent dosage when compared to typical dosages of 81 mg to about 325 mg, while demonstrating few negative side effects.

Referring to FIG. 1, in a dry powder inhalation technique, a patient can use a dry powder inhaler 10 to inhale a powder formulation of a drug, such as a NSAID. The dose is effective to reduce a risk of a thromboembolic event in the patient. An aspect of some embodiments is the realization that because the lung is an efficient filter, it generally only permits particles having a size of less than 5 μm. For example, after the drug enters the main stem bronchus 20, the drug will enter each lung 22, 24. The drug can then pass through the bronchial trees 26, 28 until reaching the individual alveoli 30 in the lungs 22, 24, which are exceedingly numerous, as discussed below. Of each long Thus, the dry powder inhaler 10 can allow the patient to self-administer a dosage of particles having a size of from about 1 μm and about 5 μm. In some embodiments, the particle size can be from about 2 μm to about 4 μm.

According to some embodiments, various types of inhalers can be used to provide the drug using a DPI or MDI delivery system. The dose administered can be effective to reduce a risk of a thromboembolic event in a patient.

For example, the dry powder inhaler 10 can comprise a mouthpiece, a reservoir for receiving the NSAID, and an actuation member for making available the NSAID for inhalation by a patient through the mouthpiece.

For example, FIGS. 2A-2F illustrate a DPI delivery device 100 having a mouthpiece 102 and a drug compartment 104. The drug compartment 104 can be inserted into an inhaler body cavity 110.

Figure 2A:
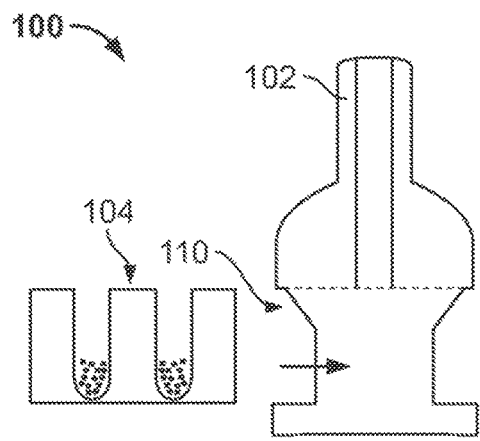
FIGS. 2A-F illustrate usages and a configuration of a dry powder inhaler, according to some embodiments.
Figure 2B:
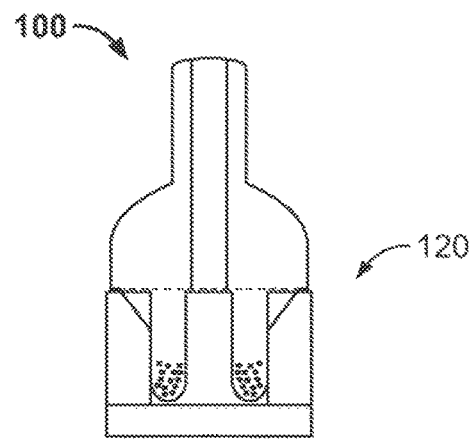
Figure 2C:
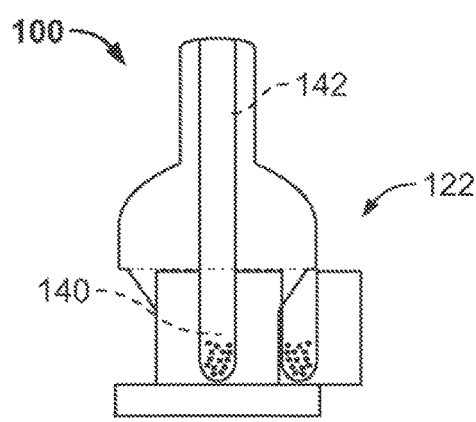
Figure 2D:
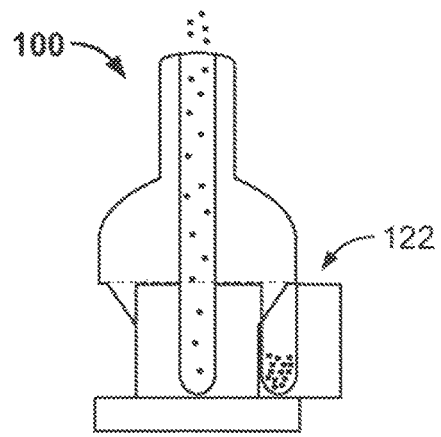

For example, as shown in FIG. 2B, the drug compartment 104 can be inserted into the body cavity 110 into a stowed position 120 for storage purposes. However, the drug compartment 104 can also be moved to a first position 122, shown in FIG. 2C, in which a first receptacle 140 of the drug compartment 104 is aligned with a mouthpiece airway 142. In this first position 122, the drug contained in the first receptacle 140 can be delivered through the mouthpiece airway 142 to be inhaled by the patient, as illustrated in FIG. 2D.

Figure 2E:
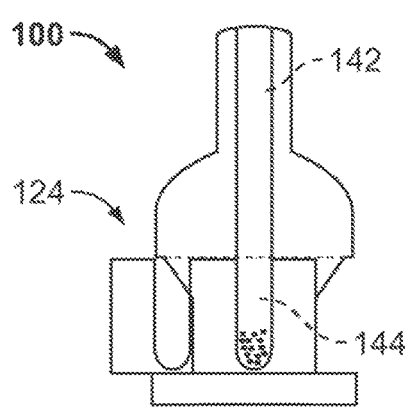
Figure 2F:
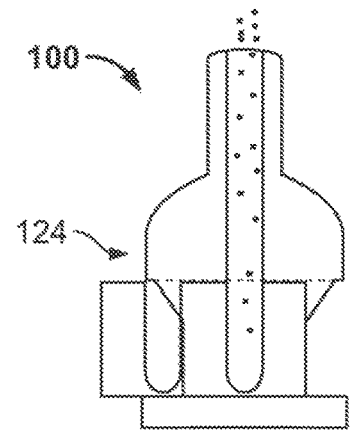

Additionally, as shown in FIG. 2E, the drug compartment 104 can be moved to a second position 124 in which a second receptacle 144 is aligned with the mouthpiece airway 142. Thus position, the drug contained in the second receptacle 144 can be inhaled by the patient, as illustrated in FIG. 2F.

In some embodiments, NSAIDs can be used in various methods and systems. In some embodiments, NSAIDs can include salicylates, i.e., the salts and esters of salicylic acid, that have anti-platelet action. Further, NSAIDs can also include one or more of the following:

Aspirin (Aspirin is a brand name; the chemical is called acetylsalicylic acid)
Celecoxib (Celebrex)
Dexdetoprofen (Keral)
Diclofenac (Voltaren, Cataflam, Voltaren-XR)
Diflunisal (Dolobid)
Etodolac (Lodine, Lodine XL)
Etoricoxib (Algix)
Fenoprofen (Fenopron, Nalfron)
Firocoxib (Equioxx, Previcox)
Flurbiprofen (Urbifen, Ansaid, Flurwood, Froben)
Ibuprofen (Advil, Brufen, Motrin, Nurofen, Medipren, Nuprin)
Indomethacin (Indocin, Indocin SR, Indocin IV)
Ketoprofen (Actron, Orudis, Oruvail, Ketoflam)
Ketorolac (Toradol, Sprix, Toradol IV/IM, Toradol IM)
Licofelone (under development)
Lomoxicam (Xefo)
Loxoprofen (Loxonin, Loxomac, Oxeno)
Lumiracoxib (Prexige)
Meclofenamic acid (Meclomen)
Mefenamic acid (Ponstel)

Meloxicam (Movalis, Melox, Recoxa, Mobic)
Nabumetone (Relafen)
Naproxen (Aleve, Anaprox, Midol Extended Relief, Naprosyn, Naprelan)
Nimesulide (Sulide, Nimalox, Mesulid)
Oxaporozin (Daypro, Dayrun, Duraprox)
Parecoxib (Dynastat)
Piroxicam (Feldene)
Rofecoxib (Vioxx, Ceoxx, Ceeoxx)
Salsalate (Mono-Gesic, Salflex, Disalcid, Salsitab)
Sulindac (Clinoril)
Tenoxicam (Mobiflex)
Tolfenamic acid (Clotam Rapid, Tufnil)
Valdecoxib (Bextra)

Other alternatives can also be used instead of a NSAID in some methods or systems disclosed herein. Such alternatives include as Plavix (clopidogrel), COX-2 inhibitors, other remedies such as Nattokinase (an enzyme (EC 3.4.21.62, extracted and purified from a Japanese food called natto). Further, other drugs that provide different beneficial effects, such as being effective to reduce a risk of a thromboembolic event in a patient, can also be used in some embodiments. Thus, the discussion of methods and systems shall apply generally to these various alternatives, although for discussion purposes, the present disclosure often refers to aspirin. It is contemplated that the methods, effects, pharmacokinetic data, and other considerations relating to aspirin can be equally applied to other NSAIDs, according to some embodiments.

Through some of the embodiments disclosed herein, the applicant has overcome the challenges acknowledged by prior teachings. In particular, the applicant has recognized that when a drug is inhaled into the lungs, the drug can be dispersed toward the alveoli. Although alveoli primarily function to exchange carbon dioxide for oxygen, alveoli also produce enzymes. Thus, inhaled substances, such as pathogens, drugs, or other chemicals, may be processed at the alveoli.

An alveolus comprises a network of elastic fibers and capillaries, resembling a woven sphere on its outer surface. The capillaries function to carry oxygen depleted blood toward the lungs and oxygen rich blood away from the lungs, via the pulmonary artery and the pulmonary vein. The interior of each alveoli comprises a thin tissue known as an alveolar lining or epithelium. Alveolar epithelium is made of two distinct types of cells, known as flat type I and type II. Flat type I cells cover most of the surface area of the epithelium and are closely spaced, allowing only small molecules to pass therebetween, such as oxygen and carbon dioxide. Type II alveolar cells aid in producing the pulmonary surfactant used in gas exchange. Further, the alveolar epithelium also comprises macrophages, which assist in disposing of fine particulate foreign matter such as dust, tar, and pathogens. Despite the diminutive size of the alveoli (being only approximately 250 µm), because an adult can have between 200 million and 400 million alveoli, the alveolar respiratory surface area can be from approximately 1,400 to about 1,600 square feet.

According to some embodiments disclosed herein, absorption of NSAIDs administered by DPI or MDI through the pulmonary capillaries and epithelium can provide an immediately effective treatment to address symptoms of thromboembolic events. One of the novel realizations of some embodiments is that the substantial first pass effect produced by oral administration of NSAIDs, such as aspirin, can be avoided through administration by dry powder inhaler. In addition, there has hitherto been no teaching or suggestion regarding the pharmacokinetics of dry powder delivery of a NSAID, such as aspirin, and the possible metabolism or inactivation of the drug as it encounters the endothelial tissue of the pulmonary capillaries.

The delivery of a NSAID by DPI or MDI is a complex and unpredictable technological area that has not provided straightforward or expected results to a person of skill in the art. Accordingly, there has been no reason for a person of skill to believe that a combination of prior systems or treatment methods could produce the embodiments disclosed herein. For example, some embodiments herein recognize an unexpected result that as a drug crosses the endothelium of pulmonary arteries and alveoli, the first pass effect is minimized and results in a much lower rate of the activation of the drug than in other drug delivery pathways.

The endothelium of the pulmonary capillaries serve as a barrier by selectively allowing materials to exit or enter the bloodstream. It would be expected that aspirin would be inactivated in the pulmonary capillaries, which are lined by endothelial cells. The endothelial cells are extremely metabolically active. Thus, a person of skill would expect that aspirin would be inactivated by the endothelium of the pulmonary capillaries. However, according to some embodiments disclosed herein, it is contemplated that as the powdered drug encounters the endothelium, the endothelium can metabolize or activate a much smaller portion of the powdered drug compared to the metabolism provided by the gut and liver. For example, after being transformed in the stomach to salicylic acid, as much as 80% of the salicylic acid is metabolized in the liver. Thus, only a small minority of the salicylic acid is bioavailable to the systemic blood stream.

However, it is contemplated that a vast majority of the salicylic acid metabolized from the inhaled aspirin powder will be bioavailable to the systemic blood stream. Thus, a dose of much less than that of a baby aspirin (e.g., less than 81 mg) can be provided by dry powder inhalation. This can provide a much lower dosage while providing a bioequivalent dosage.

Further, in accordance an aspect of some embodiments, it is contemplated that an analogous first pass effect may be experienced in the endothelium of the pulmonary capillaries. Accordingly, with regard to the provision of an inhaled dosage that is the bioequivalent of a baby aspirin administered orally, the inhaled dosage should account for some first pass effect experience through the endothelium of the pulmonary capillaries.

In accordance with some embodiments, the first pass effect through the endothelium of the pulmonary capillaries can be a minimum, which provides little overall effect on the inhaled dosage.

However, it is also contemplated that in some embodiments, the first pass effect through the endothelium of the pulmonary capillaries can be entirely negligible. Thus, the amount of the inhaled dosage need not be adjusted to compensate for first pass effect through the pulmonary capillaries.

Therefore, some embodiments recognize the unexpected result that even extremely low doses of aspirin (and likely other NSAIDs) can provide a significant therapeutic effect while providing minimal or inconsequential side effects. For example, doses as low as 1 mg, 2 mg, 3 mg, 4 mg, or 5 mg of acetylsalicylic acid can be effective in reducing the risk of a thromboembolic event. Accordingly, the net benefits increased dramatically at significantly lower doses, according to some embodiments. These results and outcomes are unexpected given the complex and unpredictable nature of drug interactions in the body, drug delivery pathways, and microscopic drug structures. Finally, no teachings or other prior references disclose a system or process for achieving therapeutically beneficial results while substantially avoiding any negative side effects using DPI or MDI drug delivery mechanisms with microscopic NSAIDs.

In accordance with some embodiments, the dry powder administration of the NSAID, such as a salicylate like acetylsalicylic acid, can comprise particles having a size of from about 1 µm to about 5 µm, as discussed above. The particles can be highly porous and demonstrate a sponge-like morphology or be a component of a carrier particle. The particles can also demonstrate a spheroidal shape, by which the shape and porous surface can serve to decrease the area of contact between particles, thereby leading to less particle agglomeration and more effective distribution throughout the lung. Dry powder technologies, such as PulmoSphere™, may be implemented in embodiments of the methods and systems disclosed herein.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

As used herein, the phrase "at least one of" preceding a series of items, with the term "and" or "or" to separate any of the items, modifies the list as a whole, rather than each member of the list (i.e., each item). The phrase "at least one of" does not require selection of at least one of each item listed; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Furthermore, to the extent that the term "include," "have," or the like is used in the description or the claims, such term is intended to be inclusive in a manner similar to the term "comprise" as "comprise" is interpreted when employed as a transitional word in a claim.

The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." Pronouns in the masculine (e.g., his) include the feminine and neuter gender (e.g., her and its) and vice versa. The term "some" refers to one or more. Underlined and/or italicized headings and subheadings are used for convenience only, do not limit the subject technology, and are not referred to in connection with the interpretation of the description of the subject technology. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

While certain aspects and embodiments of the invention have been described, these have been presented by way of example only, and are not intended to limit the scope of the invention. Indeed, the novel methods and systems described herein may be embodied in a variety of other forms without departing from the spirit thereof. The accompanying claims and their equivalents are intended to cover such forms or modifications as would fall within the scope and spirit of the invention.

The invention claimed is:

1. A method of reducing a risk of a thromboembolic event in a patient in an emergency, the method comprising:
   administering through oral inhalation to the patient a dose of a dry powder consisting essentially of acetylsalicylic acid and/or at least one pharmaceutically acceptable salt thereof, and, optionally, at least one carrier, particles of the dry powder having a median geometric diameter in a range of from 1 µm to 5 µm,
   wherein the acetylsalicylic acid and/or at least one pharmaceutically acceptable salt thereof in the dose is in a range of from 1 mg to less than 80 mg.

2. The method of claim 1, wherein the dose has less than 75 mg of the acetylsalicylic acid and/or at least one pharmaceutically acceptable salt thereof.

3. The method of claim 1, wherein the administering is a preliminary treatment in response to a symptom of the thromboembolic event.

4. The method of claim 1, wherein the median geometric diameter is in a range of from 1.7 µm to 2.7 µm.

5. The method of claim 1, wherein the acetylsalicylic acid and/or at least one pharmaceutically acceptable salt thereof in the dose administered is bioequivalent to an oral dose in a range of from 81 mg to 325 mg of acetylsalicylic acid.

6. The method of claim 1, which treats a pulmonary embolism.

7. The method of claim 1, wherein the acetylsalicylic acid is present in the dry powder.

8. The method of claim 1, wherein the acetylsalicylic acid and/or at least one pharmaceutically acceptable salt thereof in the dose is in a range of from 2 mg to 60 mg.

9. The method of claim 1, wherein the particles are spheroidal and have a sponge-like morphology.

10. A drug delivery system for reducing a risk of a thromboembolic event in an emergency, the system comprising:
- a dose of a dry powder consisting essentially of acetylsalicylic acid and/or at least one pharmaceutically acceptable salt thereof, and, optionally, at least one carrier, particles of the dry powder having a median geometric diameter in a range of from 1 μm to 5 μm; and
- a dry powder inhaler suitable for oral inhalation,
- wherein the dose has the acetylsalicylic acid and/or at least one pharmaceutically acceptable salt thereof in a range of from 1 mg to less than 80 mg, wherein the dry powder inhaler comprises a mouthpiece and a reservoir suitable for receiving the dose.

11. The system of claim 10, wherein the dose has less than 75 mg of the acetylsalicylic acid and/or at least one pharmaceutically acceptable salt thereof.

12. The system of claim 10, wherein the median geometric diameter is in a range of from 1.7 μm to 2.7 μm.

13. The system of claim 10, wherein the acetylsalicylic acid and/or at least one pharmaceutically acceptable salt thereof in the dose is in a range of from 2 mg to 60 mg.

14. The system of claim 10, wherein the particles are spheroidal and have a sponge-like morphology.

15. A method of reducing a risk of a thromboembolic event in a patient in an emergency, the method comprising:
- administering through oral inhalation to the patient a dose of a dry powder consisting of acetylsalicylic acid and/or at least one pharmaceutically acceptable salt thereof, and, optionally, at least one carrier, particles of the dry powder having a median geometric diameter in a range of from 1 μm to 5 μm,
- wherein the acetylsalicylic acid and/or at least one pharmaceutically acceptable salt thereof in the dose is in a range of from 1 mg to less than 80 mg.

16. The method of claim 15, wherein the acetylsalicylic acid and/or at least one pharmaceutically acceptable salt thereof in the dose is in a range of from 2 mg to 60 mg.

17. The method of claim 15, wherein the acetylsalicylic acid and/or at least one pharmaceutically acceptable salt thereof is present in the dry powder in a range of from 2 mg to 30 mg.

18. The method of claim 15, wherein the particles are spheroidal and have a sponge-like morphology.

19. The method of claim 15, wherein the dry powder consists of particles of the acetylsalicylic acid and/or at least one pharmaceutically acceptable salt thereof and the at least one carrier.

20. The method of claim 15, wherein the acetylsalicylic acid and/or at least one pharmaceutically acceptable salt thereof is administered in only a single dose.

21. The method of claim 15, wherein the dry powder consists of particles consisting of the acetylsalicylic acid and one carrier.

22. The method of claim 15, wherein the acetylsalicylic acid and/or at least one pharmaceutically acceptable salt thereof is not administered in a single dose.

* * * * *